United States Patent
Sheng et al.

(10) Patent No.: US 11,504,510 B2
(45) Date of Patent: Nov. 22, 2022

(54) DILATABLE BALLOON CATHETER

(71) Applicant: INNOVEX MEDICAL CO., LTD., Shanghai (CN)

(72) Inventors: Chang Sheng, Shanghai (CN); Yunteng Huang, Shanghai (CN); Zhongwei Zheng, Shanghai (CN); Wei Qian, Shanghai (CN); Hang Yan, Shanghai (CN)

(73) Assignee: Innovex Medical Co., Ltd., Shanghai (CN)

( * ) Notice: Subject to any disclaimer, the term of this patent is extended or adjusted under 35 U.S.C. 154(b) by 337 days.

(21) Appl. No.: 16/651,958

(22) PCT Filed: Oct. 17, 2017

(86) PCT No.: PCT/CN2017/106514
§ 371 (c)(1),
(2) Date: Mar. 27, 2020

(87) PCT Pub. No.: WO2019/075634
PCT Pub. Date: Apr. 25, 2019

(65) Prior Publication Data
US 2020/0254230 A1   Aug. 13, 2020

(51) Int. Cl.
*A61M 29/02*   (2006.01)
*A61M 25/09*   (2006.01)
(Continued)

(52) U.S. Cl.
CPC ............ *A61M 29/02* (2013.01); *A61M 25/09* (2013.01); *A61M 39/22* (2013.01);
(Continued)

(58) Field of Classification Search
CPC .................. A61M 29/02; A61M 25/09; A61M 2210/1025; A61M 2210/1042;
(Continued)

(56) References Cited

U.S. PATENT DOCUMENTS 5,454,788 A * 10/1995 Walker ................. A61M 25/10
604/99.04
7,713,191 B2   5/2010 Sekiguchi et al.
(Continued)

FOREIGN PATENT DOCUMENTS

CN   201182828 Y   1/2009
CN   201969170 U   9/2011
(Continued)

*Primary Examiner* — Jason E Flick
(74) *Attorney, Agent, or Firm* — Cherskov Flaynik & Gurda, LLC

(57) ABSTRACT a dilatable balloon catheter, comprising: a guide wire inserted and disposed in the inside of the catheter, an operation portion is fixedly connected to one end of the catheter, a balloon is disposed at the outer side of the catheter remote from the operation portion, the lumen of the catheter and the inner cavity of the balloon are connected by a communication structure provided on the catheter, the guide wire includes a first guide wire and a second guide wire which are separated from each other, the rear end of the first guide wire is connected to insertion-extraction structure in the rear end of the operation portion, the second guide wire is fixed to the inside of the catheter by a fixing process. The guide wire of the dilatable balloon catheter and the liquid injection lumen can share the same lumen, greatly reducing the diameter of the catheter in the present invention, so that the dilatable balloon catheter can be inserted into a narrow duct or lumen that needs to be expanded in human body through an device channel of an endoscope, and realize visualization operation.

7 Claims, 3 Drawing Sheets

(51) Int. Cl.
 *A61M 39/22* (2006.01)
 *A61M 25/00* (2006.01)
(52) U.S. Cl.
 CPC .............. *A61M 2025/0008* (2013.01); *A61M 2039/229* (2013.01); *A61M 2205/0266* (2013.01); *A61M 2210/1025* (2013.01); *A61M 2210/1042* (2013.01); *A61M 2210/1078* (2013.01)
(58) Field of Classification Search
 CPC .. A61M 2210/1078; A61M 2025/0063; A61M 2025/0186; A61M 2025/1063; A61M 2025/1068; A61M 25/00; A61M 25/10; A61B 1/01; A61B 2017/22038; A61B 2017/22045; A61B 2017/22067
 See application file for complete search history.

(56) References Cited

U.S. PATENT DOCUMENTS

| | | | |
|---|---|---|---|
| 2005/0245894 | A1 | 11/2005 | Zadno-Azizi |
| 2010/0298634 | A1 | 11/2010 | Yanuma |

FOREIGN PATENT DOCUMENTS

| | | | |
|---|---|---|---|
| CN | 204765782 U | 11/2015 | |
| CN | 204890102 U | 12/2015 | |
| CN | 106691533 A | 5/2017 | |
| CN | 106725722 A | 5/2017 | |
| CN | 107073246 A | 8/2017 | |

* cited by examiner

DILATABLE BALLOON CATHETER

PRIORITY CLAIM

The present application is a nationalization of PCT/CN2017/106514, filed on Oct. 17, 2017, presently pending. The contents of the application are hereby incorporated by reference.

FIELD OF THE INVENTION

The present invention relates to the field of medical devices, and more particularly to a dilatable balloon catheter.

BACKGROUND OF THE INVENTION

The dilatable balloon catheter of the prior art, such as, the utility model with the application number of CN201520474689.1 relates to a sealer for lithotripsy, the sealer includes a one-way valve switch, a catheter, a handle, an occlusion balloon, a protective film, a metal guide wire, a small hole; the occlusion balloon is wrapped on the outer surface of the catheter, and forms a closed capsule with the catheter, the diameter of the capsule is 5-25 mm; the occlusion balloon is oval or spherical with a length of 0.5-5 cm; a small hole is provided on the catheter wrapped around the occlusion balloon; the metal guide wire is fixedly connected to the distal end of the catheter; the metal guide wire is wrapped by the protective film; the handle is fixedly connected to the near end of the catheter; the handle is marked with stripes; the one-way valve switch is connected to the near end of the catheter; the one-way valve switch is provided with valve sheet; the one-way valve switch is connected to a syringe or an inflation valve. In the sealer for lithotripsy of the utility model, a small hole is provided on the catheter wrapped by the occlusion balloon, and the occlusion balloon and the inner lumen of the catheter are connected to each other through the small hole, and liquid can be injected into the inner lumen of the catheter and then enter the occlusion balloon to expand the balloon. However, since the two materials are different, the catheter also becomes longitudinally stretched and deformed when the occlusion balloon of this utility model is inflated by water injection and stretched longitudinally. The deformation of the catheter will cause the water-injected balloon to bend and deform, which will cause uneven surface spreading force when the balloon is swollen, increase the difficulty of surgery, reduce the effect of surgical treatment, and easily cause device damage.

The invention with application number CN201510809012.3 provides a ureteral stone movement blocking device, which consists of a catheter (1), an expandable compressed airbag (2) and a valve (3), the catheter (1) is a hollow, long tubular structure with elasticity, and is made of an elastic silicone or latex material. The front end of the catheter (1) is provided with an opening, which is located in the airbag of the expandable compressed airbag (2); the expandable compressed airbag (2) is arranged at the front end of the catheter (1), and its expansion state is ellipsoidal; the valve (3) is located at the end of the catheter (1) and is provided with a syringe inlet (4). The anterior section of the catheter (1) of the device can enter the ureter through an operating cavity so that the airbag (2) is relatively fixed in the upstream of the stone in the ureteral cavity or at the renal pelvis outlet, so as to achieve the effect of blocking the filling and expanding damage of the water flow to the kidneys, while completely blocking the pathway of any stones that may be displaced or escape to the renal pelvis. An opening is provided at the front end of the catheter (1) of the invention, and the opening is located in the airbag of the expandable compressed airbag (2); the expandable compressed airbag (2) is provided at the front of the catheter (1), which makes the guide wire impossible to be set at the front end of the compressed airbag, so the guide wire cannot be used for safe guidance and marking, thereby easily causing ureteral injury and reducing the success rate of surgery.

The utility model with the application number of CN201120001866.6 discloses a ureteral catheter with an airbag, comprising: a tube body and an airbag, wherein the airbag is located outside the tube body; two ends of the tube body are intercommunicated, and a through hole is provided in the area of the wall which is wrapped by the airbag; a baffle plate is provided in the tube body, and the baffle plate divides the space in the tube body into two independent cavities, namely a water injection cavity and a guide wire lumen, the water injection cavity is connected with the through hole, and one end of which is provided with an opening and the other end is closed, the two ends of the guide wire lumen are intercommunicated. The utility model divides the space in the tube body into two independent cavities through a baffle plate, namely a water injection cavity and a guide wire lumen, since the baffle plate is provided parallel to the axial direction of the ureteral catheter, the diameter space required by each of the two independent cavities increases the diameter of the catheter, thereby making the diameter of the catheter thicker, which is not conducive to the catheter through the device channel into the human body, and it will also further increase the patient's pain.

The above-mentioned prior art dilatable balloon catheter cannot be inserted into a device tube of endoscope due to its diameter, which also easily causes discomfort to the patient during the treatment process, and increases the difficulty of surgical operation. And, it is easy to bend and deform when the balloon is inflated with water and stretched longitudinally, thereby reducing the effect of surgical treatment and easily causing device damage.

SUMMARY OF THE INVENTION

The present invention discloses a dilatable balloon catheter, comprising: a catheter and a guide wire inserted and disposed in the inside of the catheter, wherein an operation portion is fixedly connected to one end of the catheter, the outer side of the catheter remote from the operation portion is wrapped with a balloon, the lumen of the catheter and the inner cavity of the balloon are connected by a communication structure provided on the catheter, the guide wire includes a first guide wire and a second guide wire which are separated from each other, the rear end of the first guide wire is connected to insertion-extraction structure of the operation portion, the second guide wire is fixed to the other end of the catheter by a fixing process.

Preferably, the tube body area of the catheter in the balloon is separated from each other into a first tube body and a second tube body, the rear end of the first tube body is fixedly connected to the operation portion, the outer wall of the second tube body is fixedly connected to the balloon, the cross section between the first tube body and the second tube body oppositely forms a communication passage, which serves as a communication structure to connect the lumen of the catheter and the inner cavity of the balloon, the insertion depth of the second guide wire inserted into the first tube body is greater than the separation distance between the first tube body and the second tube body when the balloon is inflated.

Further, the tube wall of the catheter in the balloon is provided with one or more through hole, and the through hole is used as a communication structure to connect the lumen of the catheter and the inner cavity of the balloon, the through hole is provided between the end portion of the second guide wire inserted into the first tube body and the connective position of the first tube body and the balloon.

Preferably, a developing ring is provided at the connective position of the front end of the balloon and the second tube body, the inside of the catheter in the area wrapped by the developing ring is closed.

Preferably, a tip catheter is provided on the side of the catheter remote from the operation portion, the second guide wire extends into the tip catheter, the distance between the end of the second guide wire in the tip catheter and the top of the tip catheter is 0.5 mm-2 mm.

Preferably, a tip catheter is provided on the side of the catheter remote from the operation portion, the second guide wire extends remote from the operation portion to the outside of the tip catheter, the portion of the second guide wire located outside the tip catheter is set as a spherical structure.

Preferably, the operation portion includes a hand-held portion; the catheter is passed through the inside of the hand-held portion to form an injection liquid channel connected to the inner cavity of the balloon.

Further, a two-way stopcock is provided at the rear end of the hand-held portion, a stopcock through-hole is provided on the plug of the two-way stopcock, when the stopcock through-hole is coaxial with the nozzle of the catheter, the liquid channel will be opened; when the stopcock through-hole is perpendicular to the nozzle of the catheter, the liquid channel will be closed.

Preferably, a scale line is provided on the outer peripheral surface of the catheter at the rear end of the balloon.

Further, the rear end of the operation portion is provided with an external thread, the external thread can be sleeved with a screw cap, the screw cap is connected to the rear end of the first guide wire as an insertion-extraction structure, the first guide wire can be pulled out by removing the screw cap.

In summary, the dilatable balloon catheter of the present invention includes a first guide wire and a second guide wire which are separated from each other, the first guide wire can be inserted and removed through the opening at the rear end of the catheter, so that the guide wire lumen and the liquid injection lumen can share the same catheter lumen, and there is no need to provide an additional liquid injection lumen, or a separate protective film on the surface of the guide wire to protect the guide wire, this greatly reduces the diameter of the dilatable balloon catheter in the present invention, so that the dilatable balloon catheter of the present invention can be inserted into a narrow duct or lumen that needs to be expanded in human body through an device channel of an endoscope, and realize visualization operation, and has good practical value.

The dilatable balloon catheter of the present invention can be used for narrow expansion of the human body's lumen such as the urinary system (ureter), the digestive system (biliary duct, pancreatic duct), the respiratory system (airway).

In order to make the above content of the present invention more obvious and understandable, preferred embodiments are described below in detail with reference to the accompanying drawings.

BRIEF DESCRIPTION OF THE DRAWINGS

The present invention will be described below with reference to the drawings.

DETAILED DESCRIPTION OF THE INVENTION

Figure 1:
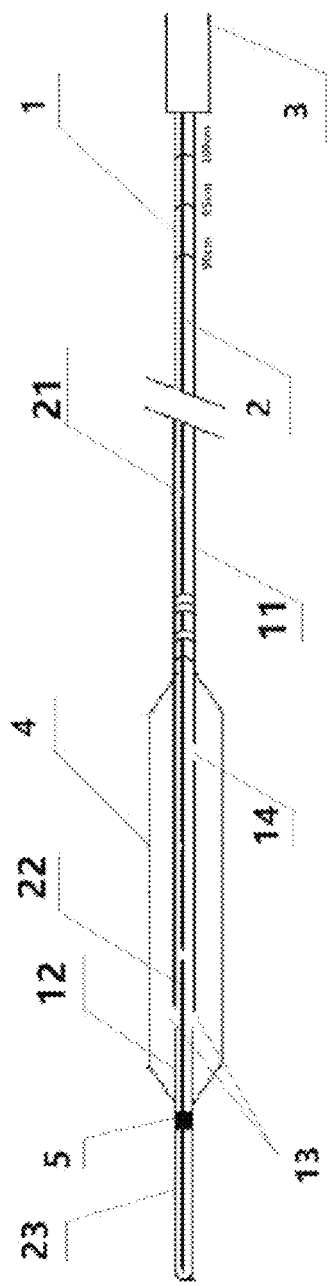
FIG. 1 is a schematic partial structural view of the dilatable balloon catheter in an embodiment of the present invention.

The following describes the embodiments of the present invention with specific embodiments.

The person skilled in the art may easily understand other advantages and effects of the present invention from the content disclosed in this specification.

The exemplary embodiments of the present invention are now described with reference to the drawings, the present invention can be implemented in many different forms and is not limited to the embodiments described herein. These embodiments are provided to disclose the present invention in detail and completely, and fully convey the scope of the present invention to the person skilled in the art. Terms used in the exemplary embodiments shown in the drawings are not intended to limit the present invention. In the drawings, the same units/elements are given the same reference numerals.

Unless otherwise stated, the terms (including scientific and technical terms) used herein have the ordinary meanings to the person skilled in the art. In addition, it can be understood that terms defined in commonly used dictionaries should be understood as having meanings consistent with the context of the related fields, and should not be construed as an idealized or overly formal meaning.

The First Embodiment

As shown in FIG. 1, the first embodiment of the present invention discloses a dilatable balloon catheter, which includes a catheter 1 and a guide wire 2 inserted and disposed in the inside of the catheter 1, an operation portion 3 is fixedly connected to one end of the catheter 1, a balloon 4 is disposed at the outer side of the catheter 1 remote from the operation portion 3, the lumen of the catheter 1 and the inner cavity of the balloon 4 are connected by a communication structure provided on the catheter 1, the guide wire 2 includes a first guide wire 21 and a second guide wire 22 which are separated from each other, the rear end of the first guide wire 21 can be detachably connected to the operation portion 3 through an insertion-extraction structure, the second guide wire 22 is fixed to the other end of the catheter 1 by a fixing process.

The guide wire 2 includes a first guide wire 21 and a second guide wire 22 which are separated from each other. The first guide wire 21 can be inserted and removed through an insertion-extraction structure provided on the operation portion 3. When the dilatable balloon catheter is inserted into human body, the guide wire is used for guiding insertion, in which the first guide wire 21 can be inserted into the lumen of catheter through an insertion-extraction structure provided on the operation portion 3, and the catheter lumen is used as a guide wire lumen to insert and dispose the guide wire. When the liquid is injected, the first guide wire 21 can be pulled out, and the catheter lumen is used as the liquid injection lumen to inject the liquid, so that the guide wire lumen and the liquid injection lumen can share the same catheter lumen, and there is no need to set another liquid injection lumen, and no need for a protective film on the surface of the guide wire to protect the guide wire. In this way, the diameter of the dilatable balloon catheter of this embodiment is greatly reduced, so that the dilatable balloon catheter of this embodiment can be inserted into the narrow duct or lumen of the human body that needs to be expanded through the device channel of the endoscope, and realize visualization operation.

Wherein, the liquid injected into the balloon is preferably physiological saline. When the physiological saline is injected into the inside of the catheter, the physiological saline enters from the rear end of the catheter 1. Since the front end of the catheter 1 is a closed structure, the physiological saline flows out of the communication structure provided on the catheter and accumulates in the balloon 4, so that the balloon 4 is inflated and expands outward. When the physiological saline is drawn out from the inside of the catheter, the balloon 4 shrinks back to the original state.

Wherein, the inside of the catheter 1 is a hollow structure, the front end of which is a closed structure and the rear end is an open structure. The guide wire 2 is inserted and disposed in the inside of the catheter 1. The lumen of the catheter 1 and the inner cavity of the balloon 4 are connected by a communication structure provided on catheter 1.

Specifically, as shown in FIG. 1, in the present embodiment, the catheter 1 is separated from each other into the first tube body 11 and the second tube body 12, the rear end of the first tube body 11 is fixedly connected to the operation portion 3, the outer wall of the second tube body 12 is fixedly connected to the balloon 4, the cross section between the first tube body 11 and the second tube body 12 oppositely forms a communication passage 13, which serves as a communication structure to connect the lumen of the catheter 1 and the inner cavity of the balloon 4.

As shown in FIG. 1, the rear end of the second guide wire 22 extends along the axis of the catheter 1 and is inserted into the inside of the first tube body 11, the insertion depth of the second guide wire 22 inserted into the first tube body 11 is greater than the separation distance between the first tube body 11 and the second tube body 12 when the balloon 4 is inflated. When the second tube body 12 is displaced longitudinally forward, the second guide wire 22 is also displaced longitudinally forward along with it, and the first tube body 11 is displaced relatively backward along the axis of the catheter 1 at this time. Since the second guide wire 22 extends from the inside of the second tube body 12 to the inside of the first tube body 11, and the insertion depth of the second guide 22 inserted into the first tube body 11 is greater than the separation distance between the first 11 and the second tube body 12 when the balloon 4 is inflated, which can ensure that the whole catheter 1 will not bend and deform at the cross section of the catheter, and provide good connection and guidance effect.

In the present embodiment, since the catheter 1 in the area of the balloon 4 is divided into two segments, the balloon 4 is inflated outwards while extending longitudinally when injecting fluid during surgery, the second tube body 12 can also be moved longitudinally forward along with it, so that the balloon 4 will not bend because of pull-up and deformation of the catheter. The balloon 4 can expand evenly after inserting a narrow duct or lumen such as a ureter in the human body, so that each side wall of the narrow duct or lumen is subjected to even force. The separation design of the two-segment catheter avoids longitudinally stretching and deforming of the catheter 1 when the balloon 4 is inflated longitudinally as a whole in the prior art. Since the catheter 1 becomes longitudinally stretched and deformed due to the different materials of the catheter 1 and the balloon 4, the deformation of catheter 1 will cause the inflated balloon to bend and deform, resulting in uneven spreading force on the surface of the balloon 4 when it expands, which will cause each side wall of the narrow duct or lumen needed to expand in human body is subjected to uneven force, resulting in poor diagnosis and treatment, causing more discomfort to the patient.

The second guide wire 22 is inserted into the first tube body 11, and the insertion depth of the second guide wire 22 inserted into the first tube body 11 is greater than the separation distance between the first tube body 11 and the second tube body 12 when the balloon 4 is inflated. It can be ensured that the second guide wire 22 will not escape from the first tube body 11 when the balloon 4 is inflated, so that the first tube body 11 and the second tube body 12 are basically maintained on the central axis of the catheter 1 when they are separated, which is further ensured that the balloon 4 will not bend and deform when it is inflated, so that the each side wall of the narrow duct or lumen that needs to be expanded is subjected to even force, which greatly improves the effect of diagnosis and treatment.

The communication passage 13 can be used as a communication structure to connect the lumen of the catheter 1 and the inner cavity of the balloon 4 so that the guide wire lumen and the liquid injection lumen can share the same catheter lumen, which greatly reduces the diameter of the dilatable balloon catheter in the present embodiment, so that the dilatable balloon catheter of this embodiment can be inserted into the narrow duct or lumen that needs to be expanded through the device channel of the endoscope, so as to achieve the visual operation, and also prevent the balloon 4 from bending and deforming when inflated by injecting fluid, which has a good therapeutic effect.

The tube wall of the first tube body 11 in the balloon 4 is further provided with one or more through hole 14, and the through hole 14 is used as a communication structure to connect the lumen of the first tube body 11 and the inner cavity of the balloon 4. The through hole 14 is provided between the end portion of the second guide wire 22 inserted into the first tube body 11 and the connective position of the first tube body 11 and the balloon 4, that is to say, the through hole 14 is provided on the side of the end portion of the second guide wire 22 inserted into the first tube body 11 near the operation portion 3.

In addition, the through hole 14 can be used as a communication structure to connect the lumen of the catheter 1 and the balloon 4, so that the guide wire lumen and the liquid injection lumen can share the same catheter lumen, which can greatly reduce the diameter of the dilatable balloon catheter in the present embodiment. Moreover, when the first guide wire 21 is drawn out of the first tube body 11 through the insertion and extraction structure connected to the operation portion 3 and then the liquid is injected, neither the first guide wire 21 nor the second guide wire 22 will block the through hole 14, which can greatly speed up the inflation of the injection fluid.

Preferably, as shown in FIG. 1, there is a developing ring 5 provided at the connective position of the front end of the balloon 4 and the second tube body 12. In the case that the device channel of the endoscope cannot be used, in order to determine the exact position of the balloon 4 moving inside the human body's duct or lumen, the X-ray imaging technology using a development ring is used, thereby monitoring the position of the balloon 4 in the tube or lumen inside the human body to achieve the purpose of diagnosis and treatment.

Similarly, The person skilled in this art can also provide a second development ring (not shown) at the connective position of the rear end of the balloon 4 and the catheter 1 as required, the setting of the two developing can more clearly determine the position of the balloon 4 in the human body's duct or lumen through X-ray contrast recording technology.

Further, the second guide wire 22 is fixedly connected to the inner side of the developing ring 5 by a fixed process, which includes glue fixation or hot melt fixation, and it is also possible to make a fixed connective position of them by using other fixed structure or fixed components.

Further, the inside of the catheter in the area wrapped by the developing ring 5 is closed, so that the injected liquid cannot enter the front of the developing ring, which can only stay inside the balloon behind the developing ring 5, which speeds up the injection speed and further shortens the time of surgery.

In the present embodiment, the material of the catheter between the developing ring 5 and the operation portion 3 may generally be PEEK, or materials such as nylon and polyamine, preferably PEEK material; PEEK material has the advantages of thin diameter and good rigidity, so that the catheter size behind the developing ring can reach 0.6 to 1.5 mm, preferably 0.7 to 1.0 mm, and the optimal 0.8 mm; the shore hardness of the catheter can reach 50 D to 95 D; preferably 80 D to 90 D. The use of PEEK material can further reduce the diameter of the catheter while ensuring the guiding effect of the catheter, thereby improving the effect of diagnosis and treatment and reducing the pain of the patient.

Preferably, as shown in FIG. 1, a side of the catheter 1 remote from the operating portion 3 may be provided with a tip catheter 23, the second guide wire 22 extending into the tip catheter 23. The distance of the leading end of the tip catheter 23 exceeding the top of the second guide wire 22 is 0.5 mm to 2 mm, that is, the distance between the end of the second guide wire 22 in the tip catheter 23 and the top of the tip catheter 23 at the front end of the developing ring is 0.5 mm-2 mm. In the embodiment of the present invention, the material of the tip catheter 23 is a soft polymer material, preferably TPU. The tip catheter 23 is made of soft material, which can avoid damage to the inner wall of the ureter caused by the insertion of hard materials, and improve the probability of successful surgery, at the same time, can guide the catheter into the human body since the tip catheter 23 also includes a part of the second guide wire 22 making the tip catheter 23 a certain degree of rigidity. Wherein, the length of the tip catheter 23 over the top of the guide wire ranges from 0.5 mm to 2 mm, the tip of the catheter is easily punctured during the insertion of the second guidewire 22 if the length is less than 0.5 mm, and the front end of the catheter will be too soft to insert if the length is greater than 2 mm, so the length of 0.5 mm-2 mm is the appropriate range.

Further, the end of the tip catheter 23 mentioned above can also be set to a spheroid structure, the smooth spherical design of the spheroid structure can guide the catheter into the inside of the human body, and can avoid the damage to the wall surface of the duct or lumen in the human body by the insertion of the elongated catheter.

As shown in FIG. 1, in the first embodiment of the present invention, a scale line is further provided on the outer peripheral surface of the catheter 1 at the rear end of the balloon 4, and the scale line can be equidistant scale line, so that the insertion depth of balloon 4 can be observed through the development of the endoscope. Traditionally, the position of the balloon is determined by determining the position of the developing ring by X-rays. Therefore, in the embodiment of the present invention, only one developing ring 5 is provided as a backup, usually, endoscopic imaging and scale are used to determine the position. The developing ring 5 assisted by X-ray is used to determine the exact position of the catheter insertion only if the scale line is not clear.

Preferably, the outside wall of the catheter 1 in front of operation section 3 is marked with a scale mark, such as 60 cm, 80 cm and 100 cm as shown in FIG. 1, for marking the distance of the catheter into the lumen of the human body, and the operator can visually observe the length of the catheter insertion through the scale mark.

Preferably, the guide wire 2 of this embodiment is a metal guide wire, the metal guide wire may be made of metal materials such as nickel-titanium alloy or stainless steel, further preferably for nickel-titanium alloy. Nickel-titanium alloy is a shape memory alloy, which is a special alloy that can automatically restore its plastic deformation to the original shape at a certain temperature. Its scalability rate is more than 20%, the fatigue life is $1\times10^7$, the damping characteristics are 10 times higher than normal springs, and its corrosion resistance is better than the best medical stainless steel at present, so it can meet the needs of various types of engineering and medical applications, which is a very good functional material. In addition to its unique shape memory function, the memory alloy also has excellent features such as wear resistance, corrosion resistance, high damping and super elasticity. The use of nickel-titanium alloy as the metal guide wire can greatly extend the service life of the device and reduce the attrition rate of the device.

Figure 3:
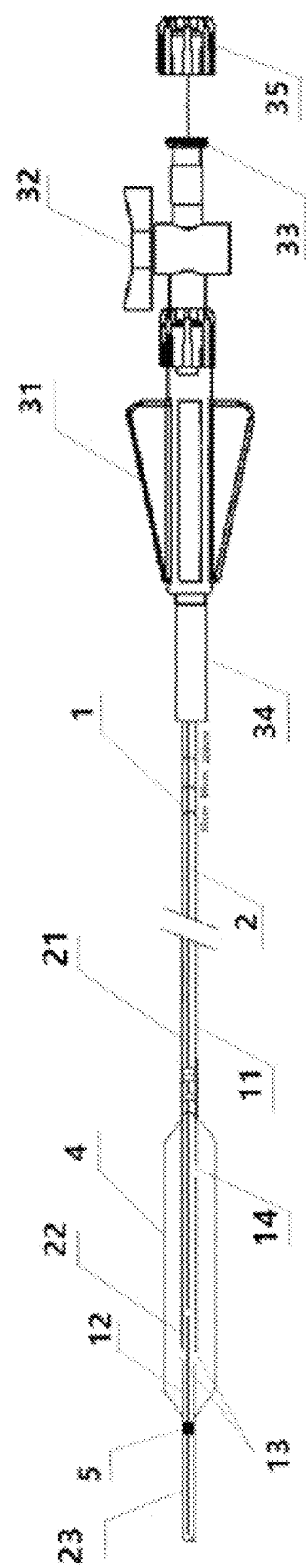
FIG. 3 is a schematic overall structure view of the dilatable balloon catheter in an embodiment of the present invention.

As shown in FIG. 3, the operation portion 3 of the dilatable balloon catheter in the present embodiment includes a hand-held portion 31, the catheter is passed through the inside of the hand-held portion 31 to form an injection liquid channel connected to the inner cavity of the balloon 4. The design of the hand-held portion 31 is convenient for the operator to hold and operate. Further, it can be seen from FIG. 3 that the hand-held portion 31 is a conical structure, that is, a shape body in which the diameter of the hand-held portion 31 decreases gradually and smoothly from the rear end to the front end. The design of the conical structure makes it easier and more comfortable for the operator to operate when holding the dilatable balloon catheter. As can be seen by the person skilled in the art, the shape of the hand-held portion 31 is not limited to the conical structure as exemplified in the present embodiment, but also can be designed in other shapes that are convenient for hand-held operation.

Preferably, a two-way stopcock 32 is provided at the rear end of the hand-held portion 31. A stopcock through-hole is provided on the plug of the two-way stopcock 32. The liquid channel will be opened when the plug of the two-way stopcock is rotated and the stopcock through-hole is coaxial with the nozzle of the catheter 1, and the liquid channel will be closed when the stopcock through-hole is perpendicular to the nozzle of the catheter 1. As shown in FIG. 3, the two-way stopcock 32 is fixed to the rear end of the hand-held portion by a nut, and a syringe is connected to the two-way stopcock 32. The liquid can be injected into the inside of the catheter lumen through the syringe when the two-way stopcock is rotated to open the liquid channel. In practice, the syringe can use 20 atmospheric pressure water injection pumps. When the two-way stopcock is rotated to close the liquid channel, it can prevent external pollutants, dust, etc. from entering the ureter through the catheter 1, causing the ureter's inner wall film infection, on the other hand, it can maintain expansion pressure to prevent the fluid in the balloon 4 from flowing out, making the shape of the occlusion balloon 4 stable. Comparing the design of the two-way stopcock 32 with the existing injection structure. The handle is easily damaged when pushing and pulling the handle constantly because the existing injection structure needs to control the opening or closing of the injection inlet by pushing or pulling through the handle or other structures wherein the connective position of the handle and the catheter is not fixed. The two-way stopcock 32 of the present invention opens and closes the liquid channel by rotating action, the structure is simple, easy to operate, and extends the service life of the device.

As shown in FIG. 3, the ends of the hand-held portion 31 and the two-way stopcock 32 are both standard Null interfaces, which can be used for syringes such as external water injection pumps. The Null interface is highly versatile and can be configured with different appliances.

Further, the rear end of the operation portion 3 is also provided with an external thread 33, the external thread 33 can be sleeved with a screw cap 35, the screw cap is connected to the rear end of the first guide wire 21 as an insertion-extraction structure, so that the operator can screw the screw cap 35 to drive the first guide wire 21 outward shift, thus pulling out the first guide wire during the operation, or screw the screw cap 35 to fix it on the external thread 33 after inserting the first guide wire. It is conceivable to the person skilled in the art that the insertion-extraction structure of the first guide wire 21 is not only limited to the screw cap provided in the present embodiment, but also includes other insertion-extraction structures that can achieve the same function.

As shown in FIG. 3, the operation portion 3 also includes a stress diffusion tube 34, the stress diffusion tube 34 is disposed at the front end of the hand-held portion 31, and the catheter 1 is passed through the stress diffusion tube 34. Its function is to avoid the stress of the base of the catheter 1 being too large to be damaged, thereby improving the operator's operating feeling, and preventing the cost loss caused by the wear of the device. The stress diffusion tube has a cylindrical shape or a hollow cone shape, the cone shape has a gradually decreasing outer diameter from back to front, which can smoothly connect with the shape of the hand-held portion 31 with more uniform force and more aesthetic appearance.

The Second Embodiment

The second embodiment of the present invention discloses a dilatable balloon catheter, which includes a guide wire 2 inserted and disposed inside of the catheter 1, an operation portion 3 is fixedly connected to one end of the catheter 1, and a balloon 4 is provided on the outer side of the distal end of the catheter 1 remote from the operation portion 3, the lumen of the catheter 1 and the inner cavity of the balloon 4 are connected by a communication structure provided on the catheter 1, the guide wire 2 includes a first guide wire 21 and a second guide wire 22 which are separated from each other, the rear end of the first guide wire 21 is connected to the insertion-extraction structure at the rear end of the operation portion 3, the second guide wire 22 is fixed to the other end of the catheter 1 by a fixing process.

Figure 2:
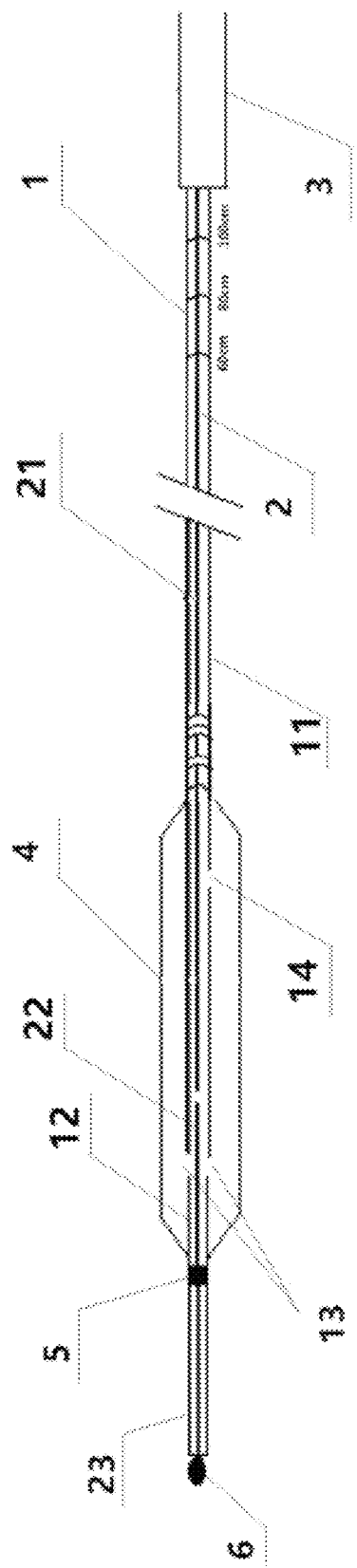
FIG. 2 is the other schematic partial structure view of the dilatable balloon catheter in an embodiment of the present invention.

This embodiment is a modification of the first embodiment. As shown in FIG. 2, this embodiment is different from the first embodiment in that a tip catheter 23 is provided on the side of the catheter 1 remote from the operation portion 3, the second guide wire 22 extends remote from the operation portion 3 to the outside of the tip catheter 23, the portion of the second guide wire 22 located outside the tip catheter 23 is set as a spherical structure 6, that is, the head of the second guide wire 22 is welded or integrated to form a spherical structure 6, which forms a guide wire with a ball head.

This can achieve the following effects: 1. Reduce the catheter material and reduce costs; 2. The thinner guide wire can better guide during the insertion process; 3. the design of the spherical structure minimizes frictional damage to the inner wall of the ureter by the insertion of a slender guide wire. Preferably, the guide wire 2 is a metal guide wire, the metal guide wire may be made of metal materials such as nickel-titanium alloy or stainless steel, further preferably for nickel-titanium alloy. Nickel-titanium alloy is a shape memory alloy, shape memory alloy is a special alloy that can automatically restore its plastic deformation to the original shape at a certain temperature. Its scalability rate is more than 20%, the fatigue life is $1\times10^7$, the damping characteristics are 10 times higher than normal springs, and its corrosion resistance is better than the best medical stainless steel at present, so it can meet the needs of various types of engineering and medical applications, and it is a very good functional material. In addition to its unique shape memory function, the memory alloy also has excellent features such as wear resistance, corrosion resistance, high damping and super elasticity. The use of nickel-titanium alloy as the metal guide wire can greatly extend the service life of the device and reduce the attrition rate of the device.

In summary, the dilatable balloon catheter of the present invention includes a first guide wire and a second guide wire which are separated from each other, the first guide wire can be inserted and removed through the opening at the rear end of the catheter, so that the guide wire lumen and the liquid injection lumen can share the same catheter lumen, and there is no need to provide an additional liquid injection lumen, or a separate protective film on the surface of the guide wire to protect the guide wire, which greatly reduces the diameter of the dilatable balloon catheter in the present invention, so that the dilatable balloon catheter of the present invention can be inserted into a narrow duct or lumen that needs to be expanded in human body through an device channel of an endoscope and realize visualization operation, and has good practical value.

The dilatable balloon catheter of the present invention can be used for narrow expansion of the human body's lumen such as the urinary system (ureter), the digestive system (biliary duct, pancreatic duct), the respiratory system (airway), but it is not limited to this. The dilatable balloon catheter of the present invention can also be used as an occluding device, for example, when the front end of the catheter 1 is inserted from the gap between the ureter wall and the stone, and reaches the upstream of the stone or even the wide renal pelvis lumen, the first guide wire can be pulled out from the opening at the rear end of the catheter, then the catheter is used as the liquid injection lumen to inject physiological saline, so that the balloon 4 entering the upstream of the stone or the renal pelvis lumen is expanded, and the balloon 4 is inflated and occluded in the ureteral lumen upstream of the stone, thereby the downstream stone fragments and the flushing liquid cannot enter the renal pelvis lumen, which can prevent the ureteral gravel from escaping. Or the near end of the catheter 1 is properly pulled back to occlude the renal pelvis outlet at the connective position of the pelvic ureter after the balloon of the renal pelvis lumen is expanded, so that any ureteral stones, stone fragments, and flushing liquid cannot enter the renal pelvis. Subsequently, the gravel treatment of ureteral stones is performed, such as laser fiber lithotripsy. The liquid in the balloon is extracted, and then the catheter is drawn out after the stone treatment is completed. In actual operation, it can be chosen to expand the balloon multiple times to adjust the balloon size, so that the balloon fits better to the inner wall of the ureter, tightly seals the ureteral stones, prevents ureteral gravel from escaping, facilitates surgical operation, and improves the success rate of lithotripsy.

In addition, the above embodiments of the present invention merely illustrate the principle and effects of the present invention, and are not intended to limit the present invention. Any person skilled in the art can modify or change the above embodiments without departing from the spirit and scope of the present invention. Therefore, all equivalent modifications or changes made by the person skilled in the art without departing from the spirit and technical ideas disclosed by the present invention should still be covered by the claims of the present invention.

The invention claimed is:

1. A dilatable balloon catheter comprising:
a catheter and a guide wire inserted and disposed in an inside of the catheter, wherein an operation portion is fixedly connected to one end of the catheter; and
a balloon which wraps an outer side of the catheter which is remote from the operation portion;
wherein a lumen of the catheter and an inner cavity of the balloon are connected by a communication structure provided on the catheter; wherein the guide wire includes a first guide wire and a second guide wire which are separated from each other, one end of the first guide wire is connected to an insertion-extraction structure of the operation portion, the second guide wire is fixed to an opposing end of the catheter by a fixing process;
wherein a tube body area of the catheter in the balloon is separated from each other into a first tube body and a second tube body, a cross section of a separation point between the first tube body and the second tube body is located within the area of the balloon, a rear end of the first tube body is fixedly connected to the operation portion, an outer wall of the second tube body is fixedly connected to the balloon, the cross section between the first tube body and the second tube body oppositely forms a communication passage, which serves as the communication structure to connect the lumen of the catheter and the inner cavity of the balloon, an insertion depth of the second guide wire inserted into the first tube body is greater than a separation distance between the first tube body and the second tube body when the balloon is inflated.

2. The dilatable balloon catheter as claimed in claim 1, wherein a tube wall of the first tube body in the balloon is provided with one or more through holes, and the one or more through holes is used as the communication structure to connect a lumen of the first tube body and the inner cavity of the balloon, the one or more through holes is provided between an end portion of the second guide wire inserted into the first tube body and a connective position of the first tube body and the balloon.

3. The dilatable balloon catheter as claimed in claim 1, wherein a developing ring is provided at a connective position of a front end of the balloon and the second tube body, the inside of the catheter in an area wrapped by the developing ring is closed.

4. The dilatable balloon catheter as claimed in claim 1, wherein a tip catheter is provided on a side of the catheter remote from the operation portion, the second guide wire extends into the tip catheter, a distance between an end of the second guide wire in the tip catheter and a distal-most end of the tip catheter is 0.5 mm-2 mm.

5. The dilatable balloon catheter as claimed in claim 1, wherein a tip catheter is provided on a side of the catheter remote from the operation portion, the second guide wire extends remote from the operation portion to an outside of the tip catheter, a portion of the second guide wire located outside the tip catheter is set as a spherical structure.

6. The dilatable balloon catheter as claimed in claim 1, wherein the operation portion includes a hand-held portion, the catheter is passed through an inside of the hand-held portion to form an injection liquid channel connected to the inner cavity of the balloon.

7. The dilatable balloon catheter as claimed in claim 5, wherein a proximal end of the operation portion is provided with an external thread, the external thread can be sleeved with a screw cap, the screw cap is connected to a proximal end of the first guide wire as the insertion-extraction structure, the first guide wire can be pulled out by removing the screw cap.

* * * * *